US 6,727,205 B2

(12) United States Patent
Brinkman

(10) Patent No.: US 6,727,205 B2
(45) Date of Patent: Apr. 27, 2004

(54) PLANT GROWTH REGULATORS AND METHODS FOR CONTROL AND/OR SUPPRESSION OF ANNUAL BLUEGRASS

(75) Inventor: Bart A. Brinkman, Salem, OR (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/164,284

(22) Filed: Jun. 6, 2002

(65) Prior Publication Data

US 2003/0013611 A1 Jan. 16, 2003

Related U.S. Application Data

(60) Provisional application No. 60/296,558, filed on Jun. 7, 2001.

(51) Int. Cl.[7] .................. A01N 43/40; A01N 37/08; A01N 37/42
(52) U.S. Cl. .................. 504/248; 504/320; 504/348
(58) Field of Search .................. 504/248, 320, 504/348

(56) References Cited

U.S. PATENT DOCUMENTS

| 3,901,687 A | * | 8/1975 | Bailey .................. 71/120 |
| 4,909,835 A | | 3/1990 | Tobler |
| 5,026,899 A | | 6/1991 | Tobler |
| 5,132,462 A | | 7/1992 | Tobler |
| 5,169,988 A | | 12/1992 | Tobler |
| 5,617,671 A | | 4/1997 | Rogers, III et al. |

FOREIGN PATENT DOCUMENTS

EP  0 945 065  9/1999

* cited by examiner

Primary Examiner—S. Mark Clardy

(57) ABSTRACT

The present invention describes compounds and compositions useful in controlling annual bluegrass weeds, including their methods of use. Included in the invention is a method of controlling annual bluegrass by applying an herbicidally effective amount of a plant growth regulator compound to an annual bluegrass plant. Also included in the present invention is a method of controlling annual bluegrass by applying an acylcyclohexanedione compound to an annual bluegrass plant.

22 Claims, No Drawings

PLANT GROWTH REGULATORS AND METHODS FOR CONTROL AND/OR SUPPRESSION OF ANNUAL BLUEGRASS

This application claims the benefit of Provisional application No. 60/296,558 filed Jun. 7, 2001.

FIELD OF THE INVENTION

The present invention relates to new herbicidal compositions and their methods of use, in particular, the present invention relates to methods of using plant growth regulators compounds and compositions for the control and/or of annual bluegrass.

BACKGROUND OF THE INVENTION

Formulations containing plant growth regulators (PGRs), such as acylcyclohexanediones and mepiquat chloride, have been developed to improve the economic yield of agricultural plants. Some PGRs have been shown to inhibit gibberellin biosynthesis resulting in the reduction of shoot height in small grains and cotton. This reduction in shoot height has a strong economic benefit since it provides for reduction of excessive vegetative growth. Although PGRs have been developed as a means to improve agricultural crop yields by retarding plant growth, PGRs are typically not used to control or suppress weeds.

One weed, annual bluegrass (*Poa annua*), is a particularly common weedy grass found in lawns, turf, and grasses used in seed production of desirable grasses, such as Kentucky bluegrass. Annual bluegrass is difficult to control in lawns and grasses because there are few selective herbicides effective against annual bluegrass. Annual bluegrass resistance to the known annual bluegrass selective herbicides is an added problem. Annual bluegrass is more than a mere menace to seed harvesters because if annual bluegrass seeds are found in desirable seed products, the value of the seed product is diminished. A need exists to develop compounds/compositions to control and/or suppress annual bluegrass.

SUMMARY OF THE INVENTION

As embodied and broadly described herein, this invention, in one aspect, relates to a method of controlling and/or suppressing annual bluegrass by applying a herbicidally effective amount of a plant growth regulator compound to an annual bluegrass plant.

The present invention also relates to, in one embodiment, a method of controlling annual bluegrass by applying an acylcyclohexanedione compound to an annual bluegrass plant.

Advantages of the invention will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

DETAILED DESCRIPTION

The present invention may be understood more readily by reference to the following detailed description of exemplary embodiments of the invention and the examples included therein.

Before the present compounds, compositions, and methods are disclosed and described, it is to be understood that this invention is not limited to specific synthetic methods of making that may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used throughout, the term "applying" is used to mean that the weed and/or the area proximate to the weed (i.e. soil, sand) has contact with the present compound(s) or composition(s) by application methods known in the art. As such, the compounds and salts of the present invention can be applied in a number of ways, for example, they can be applied, formulated or unformulated, directly to the foliage of the undesired plant or they can be sprayed on, broadcast, dusted on or applied as a cream or paste formulation or they can be applied as slow release granules (ie by injecting, shanking, chiseling or working into the soil). The compounds or compositions may be applied anytime, but application between the Boot stage and the flowering stage of the plant ("flowering" or "Anthesis") is desirable.

In general, "herbicidally effective amount" means the amount of PGR needed to achieve an observable herbicidal effect on plant growth, including the effects of plant necrosis, chlorosis, wilting, bronzing, browning, plant death, and removal, destruction, or otherwise diminishing the occurrence and activity of a plant. Desirably, the herbicidal effects result in greater than 40% control, more desirably greater than 50% control, even more desirably more than 60% control, even more desirably more than 70% control, even more desirably more than 80% control, and even more desirably more than 90% control. Such control may not be immediately apparent, but may be present after 1 days to 15 days after treatment. One of ordinary skill in the art will recognize that the potency and, therefore, an "herbicidally effective amount," can vary for the various compounds/compositions used in the invention.

"Salt" as used herein includes salts that can form with, for example, amines, metals, alkaline earth metal bases or quaternary ammonium bases, including zwitterions. Suitable metal and alkaline earth metal hydroxides as salt formers include the salts of barium, aluminum, nickel, copper, manganese, cobalt zinc, iron, silver, lithium, sodium, potassium, magnesium or calcium. Additional salt formers include chloride, sulfate, metrab, acetate, carbonate, hydride, and hydroxide.

The herbicidal compositions of present invention include a plant growth regulator (PGR) or an agronomically acceptable salt thereof. Exemplary PGRs include mepiquat chloride and acylcyclohexanedione compounds and their methods of making such as those disclosed in U.S. Pat. No. 6,083,882, U.S. Pat. No. 4,693,745 and U.S. Pat. No. 4,560,403, which are incorporated by reference in their entireties for all purposes. Any suitable acylcyclohexanedione compound may be used including, but not limited to those represented by formula I:

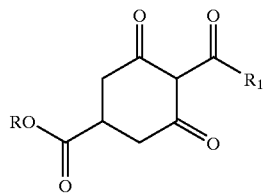

(I)

wherein R is hydrogen, an alkyl group, an alkylthioalkyl group, or a phenyl group, such that any of the groups may be substituted or unsubstitued; and $R_1$ is an alkyl group, a benzyl group, a phenoxymethyl group, a 2-thienylmethyl group, an alkoxymethyl group or an alkylthiomethyl group, such that any of the groups may be substituted or unsubstitued; or an ester or salt of the acylcyclohexanedione.

Exemplary acylcyclohexanediones include: prohexadione; prohexadione-calcium, trinexapac; trinexapac-ethyl; and 4-(n-propyl-.alpha.-hydroxymethylene)-3,5-dioxocyclohexanecarboxylic acid ethyl ester. Further exemplary PGRs include 1,1-dimethyl piperidinium chloride (mepiquat chloride).

Prohexadione, CAS Registry No. 127277-53-6, also known as 3,5-dioxo-4-propionylcyclohexanecarboxylic acid, 3,5-dioxo-4-(1-oxopropyl)cyclohexanecarboxylic acid, and also 3-hydroxy-4-prionyl-5-oxo-3-cyclohexene carboxylic acid, may be in any suitable salt or ester form. Prohexadione is represented by formula II:

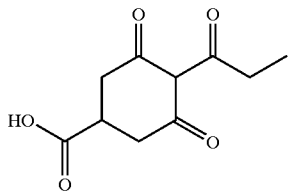

(II)

Desirable prohexadione salts include chloride, sulfate, metrab, acetate, carbonate, hydride, hydroxide, sodium, potassium, calcium, magnesium, barium, aluminum, nickel, copper, manganese, cobalt, zinc, iron and silver, with prohexadione-calcium, shown in formula III, as a more desirable salt.

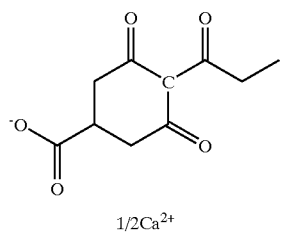

(III)

In addition to the acylcyclohexanediones of formula I, the present invention includes any suitable acylcyclohexanedione compound represented by formula IV:

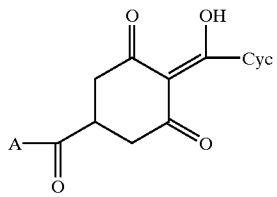

(IV)

wherein:
A is an —$OR_2$ or —$NR_3R_4$ radical;
Cyc is $C_3$–$C_6$ cycloalkyl;
$R_2$, $R_3$, and $R_4$ are each independently hydrogen, $C_1$–$C_6$ alkyl, $C_1$–$C_6$ haloalkyl, $C_2$–$C_{10}$ alkoxyalkyl, $C_2$–$C_{10}$ alkylthioalkyl, $C_3$–$C_6$ alkenyl, which is unsubstituted or substituted by halogen, $C_1$–$C_4$ alkoxy or $C_1$–$C_4$ alkylthio; $C_3$–$C_6$ alkynyl; phenyl or $C_1$–$C_6$ aralkyl, wherein the phenyl nucleus is unsubstituted or substituted by halogen, $C_1$–$C_4$ alkyl, $C_1$–$C_4$ alkoxy, $C_1$–$C_4$ haloalkyl, nitro or cyano; and
one of $R_3$ and $R_4$ is methoxy; or $R_3$ and $R_4$, together with the nitrogen atom to which they are attached, form a 5-or 6-membered heterocyclic ring system which may contain an additional oxygen or sulfur atom in the ring; and the metal or ammonium salts thereof.

Specific compounds of the immediately above noted formula, for use in practicing embodiments of the invention include trinexapac, also known as 4-cyclopropyl(hydroxy)methylene-3,5-dioxocyclohexanecarboxylic acid, which is depicted in formula V, and its ethyl ester, trinexapac-ethyl, also known as ethyl 4-cyclopropyl(hydroxy)methylene-3,5-dioxocyclohexanecarboxylate and ethyl 4-(cyclopropylhydroxymethylene)-3,5-dioxocyclohexanecarbocylate, which is represented in formula VI.

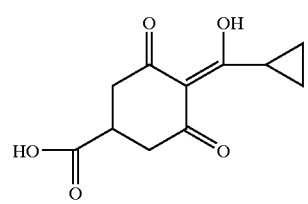

(V)

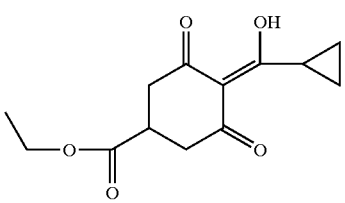

(VI)

The PGR compounds may be applied formulated or unformulated. Typical formulations contain the acylcyclohexanedione in a range from 0.1 parts to 100 parts by weight and may also contain a carrier. The carrier may be any natural or synthetic organic or inorganic ingredient that facilitates dispersion of the composition or compound and contact with the plant. The carrier may be solid (e.g. clays, synthetic silicates, silica, resins, waxes, kaolin, bentonite, dolomite, calcium carbonate, talc, powdered magnesia, Fuller's earth, gypsum, diatomaceous earth, China clay, and combinations thereof); liquid (e.g. water, aqueous solutions, N-methylpyrrolidone, kerosene, cyclohexanone, methylethyl ketone, acetonitrile, methanol, ethanol, isopropyl alcohol, acetone, butyl cellosolved, 2-ethyl-1hexanol, cyclohexanone, methyl cellulose, polyvinyl alcohol, sodium lignin sulfonates, polymeric alkyl naphthalene sulfonates, sodium naphthalene sulfonate, polymethylene bisnaphthalenesulfonate, sodium N-methyl-N-(long chain acid) laureates, hydrocarbons and other water-immiscible ethers, esters and ketones, and combinations thereof); or a combination of solid and liquid carriers.

Formulations useful in the present invention may also contain one or more surfactants to increase the biological effectiveness of the active ingredient. Suitable surface active ingredients include surfactants, emulsifying agents, and wetting agents. A wide range of surfactants is available and can be selected readily by those skilled in the art from "The Handbook of Industrial Surfactants," 2nd Edition, Gower (1997), which is incorporated herein by reference in its entirety for all purposes. There is no restriction on the type or chemical class of surfactant(s) that can be used. Nonionic, anionic, cationic and amphoteric types, or combinations of more than one of these types, are all useful in particular situations.

Among nonionic surfactants, exemplary classes include polyoxyethylene alkyl, alkyne, alkynyl or alkylaryl ethers, such as polyoxyethylene primary or secondary alcohols, alkylphenols or acetylenic diols; polyoxyethylene alkyl or alkyne esters, such as ethoxylated fatty acids; sorbitan alkylesters, whether ethoxylated or not; glyceryl alkylesters; sucrose esters; and alkyl polyglycosides. Exemplary anionic surfactant classes include fatty acids, sulfates, sulfonates, and phosphate mono- and diesters of alcohols, alkylphenols, polyoxyethylene alcohols and polyoxyethylene alkylphenols, and carboxylates of polyoxyethylene alcohols and polyoxyethylene alkylphenols. These can be used in their acid form but are more typically used as salts, for example sodium, potassium or ammonium salts.

Cationic surfactants classes include polyoxyethylene tertiary alkylamines or alkenylamines, such as ethoxylated fatty amines, quaternary ammonium surfactants and polyoxyethylene alkyletheramines. Representative specific examples of such cationic surfactants include polyoxyethylene (5) cocoamine, polyoxyethylene (15) tallowamine, distearyldimethylammonium chloride, N-dodecylpyridine chloride and polyoxypropylene (8) ethoxytrimethylammonium chloride. Many cationic quaternary ammonium surfactants of diverse structures are known in the art to be useful in combination with herbicides and can be used in compositions contemplated herein.

Suitable emulsifying agents and wetting agents include, but are not limited to, ionic and nonionic types such as polyacrylic acid salts, lignosulphonic acid salts, phenolsulphonic or naphthalenesulphonic acids, products of polycondensation of ethylene oxide with fatty alcohols, fatty acids or fatty amines, substituted phenols (especially alkylphenols or arylphenols), sulphonosuccinic acid ester salts, taurine derivatives (especially alkyl taurates), phosphoric esters of alcohols or products of polycondensation of ethylene oxide with phenols, esters of fatty acids with polyhydric alcohols, and derivatives having sulphate, sulphonate and phosphate groups, of the compounds above.

Compositions of this invention may also contain other active ingredients, for example fertilizers such as ammonium nitrate, urea, potash, and superphosphate; phytotoxicants and plant growth regulators; safeners; and pesticides. These additional ingredients may be used sequentially or in combination with the above-described compositions. For example, the plant(s) may be sprayed with a composition of this invention either before or after being treated with other active ingredients. Such sequential applications may be performed by applying the combination of active ingredients individually within a one day period or less, such as separate applications of the individual compounds within less than 1 hour, less than 5 hours, less than 10 hours, less than 14 hours, or less than 17 hours.

Other optional components may be admixed with the present compositions to facilitate the application and/or effectiveness of the active ingredient. To this end, optional components that may be added include antifoaming agents including silicone based antifoaming agents; thickening agents such as fumed silica; antimicrobial agents; antioxidants; buffers; dyes; perfumes; stabilizing agents; and antifreezing agents. Exemplary antifreezing agents include but are not limited to, glycols such as propylene glycol and ethylene glycol, N-methylpyrrolidone, cyclohexanone, and alcohols such as ethanol and methanol.

Compositions of the present invention may be present in any effective formulation, including, but not limited to, dusting powders or granules; dispersible powders, granules or grains; aqueous dispersions; or emulsions.

Powders, including dusting powders or granules and dispersible powders, granules or grains contain at least one active ingredient and an inert solid extender or carrier, such as kaolin, bentonite, dolomite, calcium carbonate, talc, powdered magnesia, Fuller's earth, gypsum, diatomaceous earth and China clay. Dispersible powders, granules and grains typically also include one or more wetting and dispersing agents, such as surfactants.

The composition of this invention may be made up as granules comprising 0.5 to 40%, preferably 2 to 30% by weight of the active compound of this invention as active ingredient; 1 to 20%, preferably 2 to 10% by weight of the surfactant; and 40 to 98.5%, preferably 20 to 96% by weight of solid carrier. Formulated into a dust, the composition may include 0.5 to 40%, preferably 1 to 35% by weight of the active ingredient; and 99.5 to 60%, preferably 99 to 65% by weight of finely divided solid carrier.

The composition of this invention may also be formulated into a paste comprising 0.1 to 20%, preferably 1 to 10% by weight of the active ingredient, 1 to 20%, preferably 2 to 10% by weight of surfactant; and 60 to 98.9%, preferably 80 to 97% by weight of paste base. In a wettable powder formulation, the composition typically includes 5 to 95%, preferably 10 to 50% by weight of the new compounds of this invention as active ingredient; 1 to 20%, preferably 5 to 10% by weight of surfactant; and 4 to 44%, preferably 40 to 85% by weight of solid carrier, the solid carrier being preferably ammonium sulfate.

The aqueous dispersions or emulsions may be prepared by dissolving the active ingredient in an organic solvent optionally containing wetting, dispersing or emulsifying agent(s) and then adding the mixture to water which may also contain wetting, dispersing or emulsifying agents(s). Suitable organic solvents are kerosene, cyclohexanone, methylethyl ketone, acetone, methanol, acetonitrile, and the like. The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s).

Typical liquid solutions include the active ingredient, a carrier, and optionally, a surface active agent. The dilute solutions of the present compositions generally contain about 0.1 to about 50 parts active ingredient, about 0.25 to about 50 parts carrier, and about 0 to about 94 parts surface active agent, all parts being by weight based on the total weight of the composition. Similarly, the concentrated compositions typically include about 40 to about 95 parts active ingredient, about 5 to about 25 parts carrier, and about 0 to about 20 parts surface active agent.

Emulsifications are usually solutions of active ingredients in water-immiscible or partially water-immiscible solvents as the carrier together with at least one surface active agent. Suitable solvents for the active ingredients of this invention include, but are not limited to, hydrocarbons and water-immiscible ethers, esters or ketones. The emulsification compositions generally contain from S to 95%, preferably 20 to 70% by weight of the active compound of this invention as active ingredient; 1 to 40%, preferably 5 to 20% by weight of surfactant; and 4 to 94%, preferably 10 to 75% by weight of liquid carrier.

An herbicidally effective amount of the composition will vary according to the prevailing conditions such as weather, plant species, feed pressure, growth stage, mode of application, cultivation practice and the like. The rate of application of the compound and/or composition of this invention may be in the range of 5 g to 1000 g per hectare, desirably 25 g to 600 g per hectare as the active ingredient, more desirably 50 g to 500 g per hectare.

The compounds useful in the present invention may be readily synthesized using techniques generally known to synthetic organic chemists. In general, the compounds and compositions may also be purchased commercially. The compositions may be prepared in known manner, for example by homogeneously mixing or grinding the active ingredients with other ingredients. Additional components may be admixed with the composition at any point during the process, including during and/or after any mixing.

When operating in accordance with the present invention, the annual bluegrass or area proximate to the annual bluegrass is contacted with an herbicidally effective amount of the compound or composition of the present invention. The application of such compositions to terrestrial plants can be carried out by conventional methods, e.g. power dusters, boom and hand sprayers and spray dusters. The compositions can also be applied from airplanes as a dust or a spray because of their effectiveness at low dosages.

Experimental:

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, percent is percent by weight given the component and the total weight of the composition, temperature is in ° C. or is at ambient temperature, and pressure is at or near atmospheric.

EXAMPLE 1

Evaluation of the Effects of PGRs as Measured by Weed Control

In this evaluation, annual bluegrass (Poa Annua) was grown, and the compounds were applied at various growth stages of the annual bluegrass as depicted in Table Ia using a randomized complete block design of four replications with ten treatments including one untreated control. The compounds were applied using water as the carrier. The results shown in Table Ib depict control of annual bluegrass, which includes browning, necrosis, melt-down and plant death. The results shown in Table Ic depict the amount of seeds on the plants and on the ground for the various treatments.

TABLE Ia

Growth Stages for Applications

| | | | Application Time | | | |
|---|---|---|---|---|---|---|
| Development | A | B | C | D | E | F |
| No. Leaves or Size | 1–2 | 1–3 | 3–6 | 3–7 | 7–9.5 cm tall | 14–18.5 cm tall |
| Growth Stage | Seedling | Seedling | Tillering | Tillering | Flowering | Flowering to Soft Dough |
| Day of Treatment | 1 (First Treatment) | 15 | 35 | 51 | 136 | 155 |

TABLE Ib

Percent Control of Annual BlueGrass

| | | | % Control at Days After First Treatment (DAT) | | | | | |
|---|---|---|---|---|---|---|---|---|
| | | Application | | | | | | |
| App Time | Active Ingredient | Rate in lb/A (kg/ha) | 17 DAT | 43 DAT | 77 DAT | 151 DAT | 172 DAT | 204 DAT |
| A | Prohexadione-Calcium | 0.125 (140) | 0 | 0 | 0 | 0 | 0 | 0 |
| A | Glufosinate-Ammonium | 0.375 (420) | 80 | 80 | 74 | 33 | 3 | 0 |

TABLE Ib-continued

Percent Control of Annual BlueGrass

| App Time | Active Ingredient | Application Rate in lb/A (kg/ha) | % Control at Days After First Treatment (DAT) | | | | | |
|---|---|---|---|---|---|---|---|---|
| | | | 17 DAT | 43 DAT | 77 DAT | 151 DAT | 172 DAT | 204 DAT |
| A + B | Prohexadione-Calcium | A = 0.125 (140) + B = 0.125 (140) | 0 | 0 | 0 | 0 | 0 | 0 |
| C | Prohexadione-Calcium | 0.125 (140) | | 0 | 0 | 0 | 0 | 0 |
| C | Glufosinate-Ammonium | 0.375 (420) | | 10 | 96 | 74 | 45 | 18 |
| C + D | Prohexadione-Calcium | C = 0.125 (140) + D = 0.125 (140) | | | 0 | 0 | 0 | 0 |
| E | Glufosinate-Ammonium | 0.375 (420) | | | | 93 | 65 | 8 |
| F | Prohexadione-Calcium | 0.250 (280) | | | | | 60 | 95 |
| F | Trinexapac-Ethyl | 0.360 (404) | | | | | 60 | 94 |
| Control | None | None | 0 | 0 | 0 | 0 | 0 | 0 |

Notes:
Prohexadione-Calcium (calsium 3,5-dioxo-4-(1-oxopropyl)cyclohexanecarboxylate) is formulated as 27.5% dry formulation
Glufosinate-Ammonium (2-amino-4-(hydoxymethylphosphinyl)butanoic acid) is formulated as a solution concentrate (SC) of 1 lb/gal (120 g/l)
Trinexapac-Ethyl (ethyl 4-cyclopropyl(hydroxy)methylene-3,5-dioxocyclohexanecarboxylate) is fromulated as a SC of 2.1 lb/gal (252 g/l)

TABLE Ic

Seed/Biomass Effect on Annual BlueGrass

| | Effect at Day 212 | | | | |
|---|---|---|---|---|---|
| App Time | Seeds on Plant (seeds/ 0.3 g) | Seeds on Ground (seeds/ 0.3 g | Seeds on Plant (g/5 sq ft) | Seeds on Ground (g/5 sq ft) | Biomass Dry Weight (g/5 sq ft) |
| E (Glufosinate-Ammonium) | 1000 | 816 | 32 | 34 | 184 |
| F (Prohexa-dione-Calcium) | 822 | 583 | 34 | 50 | 188 |
| F (Trinexapac-Ethyl) | 859 | 665 | 35 | 48 | 183 |
| Control (None) | 864 | 669 | 37 | 30 | 251 |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of controlling annual bluegrass comprising applying an herbicidally effective amount of at least one plant growth regulator compound to an annual bluegrass plant.

2. The method of claim 1, wherein the plant growth regulator is selected from the group consisting of an acyl-cyclohexanedione compound and mepiquat chloride.

3. The method of claim 2, wherein the acylcyclohexanedione compound is trinexapac.

4. The method of claim 3, wherein the trinexapac is trinexapac-ethyl.

5. The method of claim 2, wherein the acylcyclohexanedione compound is prohexadione.

6. The method of claim 5, wherein the prohexadione is prohexadione-calcium.

7. The method of claim 2 wherein the acylcyclohexanedione is applied at a rate of about g per hectare to about 600 g per hectare.

8. The method of claim 1, wherein the plant growth inhibitor is formulated as a dusting powder or granule; dispersible powder, granule or grain; aqueous dispersion; or emulsion.

9. The method of claim 1, wherein the compound is applied during flowering.

10. The method of claim 1, wherein the plant growth regulator is applied between the Boot stage and the Anthesis stage of growth.

11. A method of controlling annual bluegrass comprising applying an acylcyclohexanedione compound to an annual bluegrass plant.

12. The method of claim 11, wherein the acylcyclohexanedione compound is trinexapac.

13. The method of claim 12, wherein the trinexapac is trinexapac-ethyl.

14. The method of claim 11, wherein the plant growth regulator is applied between the Boot stage and the Anthesis stage of growth.

15. The method of claim 11, wherein the compound is applied during flowering.

16. The method of claim 11, wherein the plant growth inhibitor is formulated as a dusting powder or granule, dispersible powder, granule or grain, aqueous dispersion, or emulsion.

17. The method of claim 11, wherein the acylcyclohexanedione is applied at a rate of about 25 g per hectare to about 600 g per hectare.

18. The method of claim 11, wherein the method induces necrosis.

19. The method of claim 11, wherein the acylcyclohexanedione compound is prohexadione.

20. The method of claim 19, wherein the acylcyclohexanedione compound is prohexadione-calcium.

21. A method of suppression annual bluegrass comprising applying an effective amount of at least one plant growth regulator compound to an annual bluegrass plant.

22. The method of claim 21, wherein the plant growth regulator is selected from the group consisting of an acylcyclohexanedione compound and mepiquat chloride.

* * * * *